US012333712B2

(12) United States Patent
Konno et al.

(10) Patent No.: US 12,333,712 B2
(45) Date of Patent: Jun. 17, 2025

(54) CONTROL DEVICE, CONTROL METHOD, AND CONTROL PROGRAM

(71) Applicant: FUJIFILM CORPORATION, Tokyo (JP)

(72) Inventors: Shinichiro Konno, Kanagawa (JP); Yoshie Fujimoto, Kanagawa (JP); Shunsuke Kodaira, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 304 days.

(21) Appl. No.: 17/486,952

(22) Filed: Sep. 28, 2021

(65) Prior Publication Data

US 2022/0101524 A1 Mar. 31, 2022

(30) Foreign Application Priority Data

Sep. 30, 2020 (JP) ................................ 2020-166462

(51) Int. Cl.
*A61B 6/00* (2024.01)
*G06T 7/00* (2017.01)

(52) U.S. Cl.
CPC .. *G06T 7/0012* (2013.01); *G06T 2207/30068* (2013.01)

(58) Field of Classification Search
CPC ......... G06T 7/0012; G06T 2207/30068; A61B 6/025; A61B 6/06; A61B 6/502; A61B 6/0414
See application file for complete search history.

(56) References Cited

U.S. PATENT DOCUMENTS

| 9,820,705 B2* | 11/2017 | Kim ........................ G21K 1/04 |
| 10,238,343 B2* | 3/2019 | Goossen ................ A61B 5/708 |
| 2006/0029268 A1* | 2/2006 | Endo ...................... A61B 6/463 |
| | | 382/132 |
| 2009/0299218 A1 | 12/2009 | Holler et al. |

(Continued)

FOREIGN PATENT DOCUMENTS

| JP | 2007-236805 A | 9/2007 |
| JP | 2008-086389 A | 4/2008 |

(Continued)

OTHER PUBLICATIONS

English language translation of the following: Office action dated Apr. 18, 2023 from the JPO in a Japanese patent application No. 2020-166462 corresponding to the instant patent application. This office action translation is submitted now in order to supplement the understanding of the cited references which are being disclosed in the instant Information Disclosure Statement.

*Primary Examiner* — Nay A Maung
*Assistant Examiner* — Dustin Bilodeau
(74) *Attorney, Agent, or Firm* — SOLARIS Intellectual Property Group PLC

(57) ABSTRACT

A control device including: at least one processor, wherein the processor controls an image projection unit that projects a projection image onto a projection surface of a compression member in a mammography apparatus which irradiates a breast compressed by the compression member with radiation to capture a radiographic image such that a range of an irradiation field of the radiation is displayed by the projection image.

13 Claims, 11 Drawing Sheets

(56) References Cited

U.S. PATENT DOCUMENTS

| | | | |
|---|---|---|---|
| 2014/0146944 A1* | 5/2014 | Sato | A61B 6/542 378/62 |
| 2014/0328458 A1 | 11/2014 | Erhard et al. | |
| 2014/0334598 A1* | 11/2014 | Park | A61B 6/502 378/37 |
| 2017/0172531 A1* | 6/2017 | Sugiyama | A61B 6/0414 |
| 2017/0367671 A1* | 12/2017 | Arai | A61B 6/502 |
| 2020/0253572 A1 | 8/2020 | Nakayama | |

FOREIGN PATENT DOCUMENTS

| | | | |
|---|---|---|---|
| JP | 2009-285345 A | 12/2009 | |
| JP | 2014-533548 A | 12/2014 | |
| JP | 2017-113540 A | 6/2017 | |
| JP | 2020-127650 A | 8/2020 | |
| WO | 2020/069031 A1 | 4/2020 | |

* cited by examiner

FIG. 6A

| COMPRESSION PLATE IDENTIFIER | ANGLE INFORMATION OF ARM PORTION | IRRADIATION FIELD RANGE INFORMATION |
|---|---|---|
| ****** | +36° TO +146° | COORDINATES: (AA,BB), (CC,DD) |
| ****** | LESS THAN ±36°, EQUAL TO OR GREATER THAN ±146° | COORDINATES: (EE,FF), (GG,HH) |
| ****** | −36° TO −146° | COORDINATES: (II,JJ), (KK,LL) |
| ¥¥¥¥¥¥ | +36° TO +146° | COORDINATES: (QQ,RR), (SS,TT) |

FIG. 6B

| COMPRESSION PLATE IDENTIFIER | ANGLE INFORMATION OF ARM PORTION | IRRADIATION FIELD RANGE INFORMATION |
|---|---|---|
| ****** | | COORDINATES: (MM,NN), (OO,PP) |
| ¥¥¥¥¥¥ | | COORDINATES: (UU,VV), (WW,XX) |

CONTROL DEVICE, CONTROL METHOD, AND CONTROL PROGRAM

CROSS-REFERENCE TO RELATED APPLICATIONS

The present application claims priority under 35 U.S.C. § 119 to Japanese Patent Application No., 2020-166462 filed on Sep. 30, 2020. The above application is hereby expressly incorporated by reference, in its entirety, into the present application.

BACKGROUND

Technical Field

The present disclosure relates to a control device, a control method, and a control program.

Description of the Related Art

A mammography apparatus is known which irradiates a breast compressed by a compression member with radiation to capture a radiographic image. In a case in which a projection image is projected to perform imaging, information or the like for assisting the imaging may be displayed. For example, JP2008-086389A discloses a technique that displays a skin line of the breast on a liquid crystal display (LCD) and displays a projection image thereof on a projection surface of a compression member.

Further, in the mammography apparatus, there is known a technique which emits visible light to project the range of the irradiation field, thereby indicating the range of the irradiation field of radiation. For example, JP2008-086389A discloses a technique which indicates the irradiation field of radiation using visible light emitted from a projection light source.

SUMMARY

In the technique disclosed in JP2008-086389A, light is emitted for both the projection of a projection image and the projection of the irradiation field. Therefore, in a case in which the projection image and the irradiation field are projected at the same time, light overlaps. As a result, in some cases, the projection image and the irradiation field are unrecognizable. For example, in a case in which visible light for projecting the range of the irradiation field is emitted while the projection image is being projected, display corresponding to the projection image may not be visible due to the emitted visible light. Therefore, there is a demand for a technique that enables the user to recognize the range of the irradiation field without projecting the irradiation field.

The present disclosure has been made in view of the above-mentioned problems, and an object of the present disclosure is to provide a control device, a control method, and a control program that enable a user to recognize a range of an irradiation field without projecting the irradiation field.

In order to achieve the above object, according to a first aspect of the present disclosure, there is provided a control device comprising at least one processor. The processor controls an image projection unit that projects a projection image onto a projection surface of a compression member in a mammography apparatus which irradiates a breast compressed by the compression member with radiation to capture a radiographic image such that a range of an irradiation field of the radiation is displayed by the projection image.

According to a second aspect of the present disclosure, in the control device according to the first aspect, the processor may acquire irradiation field information indicating a size of the range of the irradiation field of the radiation and perform control such that the range of the irradiation field of the radiation is displayed by the projection image in a case in which a size of a display image displayed on the projection surface by the projection image is different from the size of the range of the irradiation field indicated by the irradiation field information.

According to a third aspect of the present disclosure, in the control device according to the first aspect, the processor may perform control to display the range of the irradiation field such that a size of a display image displayed by the projection of the projection image is equal to a size of the range of the irradiation field.

According to a fourth aspect of the present disclosure, in the control device according to the first aspect, the processor may acquire irradiation field information indicating a size of the range of the irradiation field of the radiation and perform control to change a size of a display image displayed by the projection of the projection image depending on the size of the range of the irradiation field in a case in which the size of the range of the irradiation field indicated by the irradiation field information is changed.

According to a fifth aspect of the present disclosure, in the control device according to the first aspect, the processor may perform control such that a projection image including irradiation field information indicating the range of the irradiation field is projected to display the range of the irradiation field.

According to a sixth aspect of the present disclosure, in the control device according to the first aspect, the projection image may include guide information for guiding a shape of the breast in a compressed state, and the processor may perform control such that the guide information is different inside and outside the range of the irradiation field to display the range of the irradiation field.

According to a seventh aspect of the present disclosure, in the control device according to the sixth aspect, the processor may perform control such that the guide information is not displayed outside the range of the irradiation field for the difference.

According to an eighth aspect of the present disclosure, in the control device according to the first aspect, the projection image may include imaging information, and the processor may perform control to display the imaging information at the same position regardless of the range of the irradiation field.

According to a ninth aspect of the present disclosure, in the control device according to the eighth aspect, the imaging information may include at least information indicating a compression pressure of the compression member against the breast.

According to a tenth aspect of the present disclosure, in the control device according to the first aspect, the processor may control an irradiation field projection unit which projects visible light within the range of the irradiation field to indicate the range of the irradiation field such that the range of the irradiation field is displayed in a case in which the image projection unit does not project the projection image.

According to an eleventh aspect of the present disclosure, in the control device according to the first aspect, the projection image may include imaging information. In a case in which an instruction for an irradiation field projection unit, which projects visible light within the range of the irradiation field to indicate the range of the irradiation field, to display the range of the irradiation field is received during the projection of the projection image by the image projection unit, the processor may perform control to switch to a projection image for displaying the imaging information outside the range of the irradiation field or control to switch a projection position of the projection image to a state in which the imaging information is displayed outside the range of the irradiation field.

According to a twelfth aspect of the present disclosure, in the control device according to the eleventh aspect, the projection image may further include guide information for guiding a shape of the breast in a compressed state, and the processor may perform control that a position where the guide information is displayed remains the same.

In addition, in order to achieve the above object, according to a thirteenth aspect of the present disclosure, there is provided a control method comprising controlling an image projection unit that projects a projection image onto a projection surface of a compression member in a mammography apparatus which irradiates a breast compressed by the compression member with radiation to capture a radiographic image such that a range of an irradiation field of the radiation is displayed by the projection image.

Moreover, in order to achieve the above object, according to a fourteenth aspect of the present disclosure, there is provided a non-transitory computer-readable storage medium storing a control program that causes a computer to perform a process of controlling an image projection unit that projects a projection image onto a projection surface of a compression member in a mammography apparatus which irradiates a breast compressed by the compression member with radiation to capture a radiographic image such that a range of an irradiation field of the radiation is displayed by the projection image.

According to the present disclosure, it is possible to enable the user to recognize the range of the irradiation field without projecting the irradiation field.

BRIEF DESCRIPTION OF THE DRAWINGS

Exemplary embodiments according to the technique of the present disclosure will be described in detail based on the following figures, wherein:

FIG. 6A illustrates an example of irradiation field information corresponding to irradiation field range information in a case in which the size of the irradiation field is smaller than the size of the projection surface.

FIG. 6B illustrates an example of irradiation field information corresponding to irradiation field range information in a case in which the size of the irradiation field is equal to the size of the projection surface.

DETAILED DESCRIPTION

Hereinafter, embodiments of the present disclosure will be described in detail with reference to the drawings. In addition, each of the embodiments does not limit the present disclosure.

Figure 1:
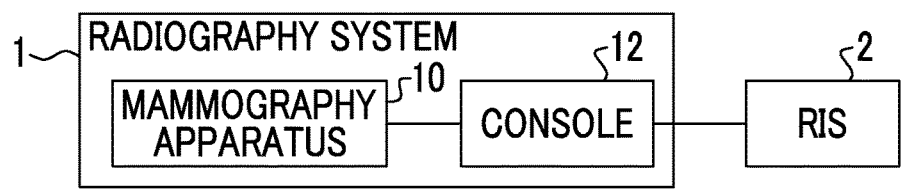
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of a control device according to the present disclosure.

Figure 2A:
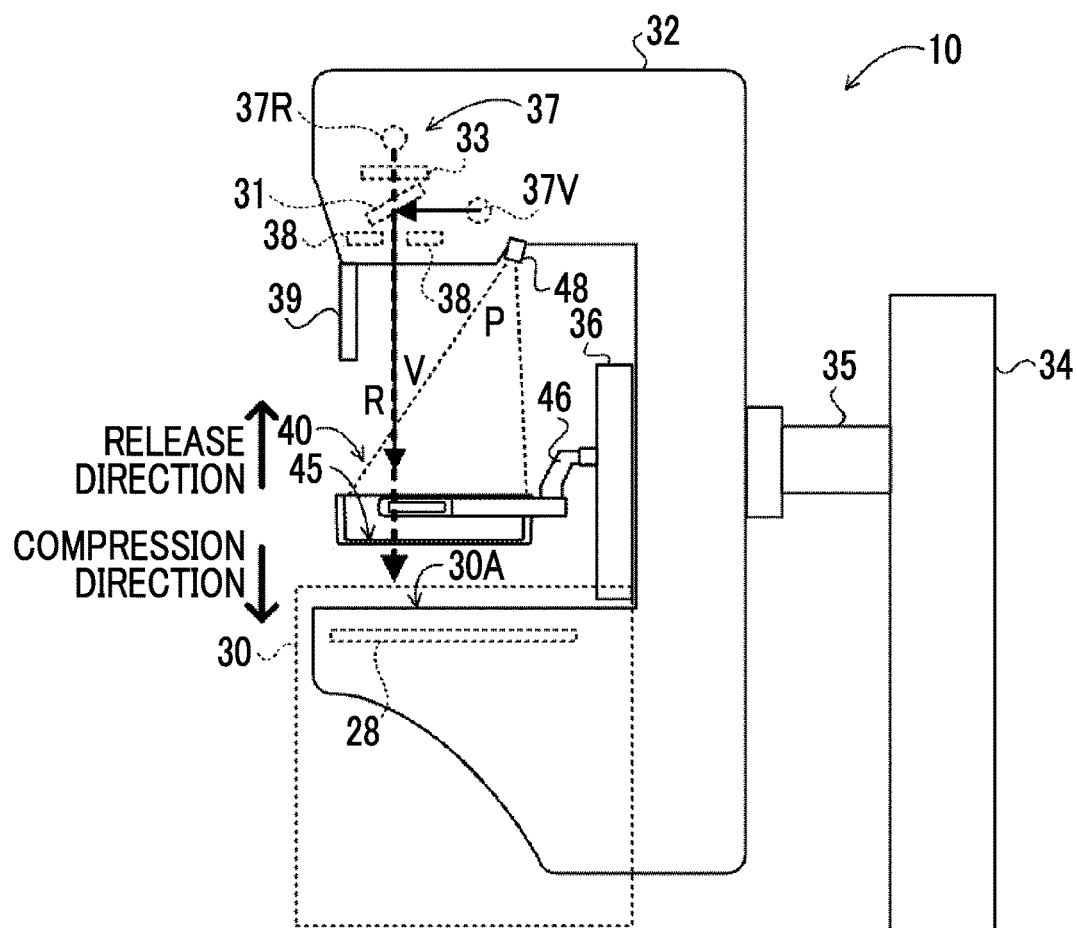
FIG. 2A is a side view illustrating an example of the outward appearance of a mammography apparatus according to the embodiment.
Figure 3:
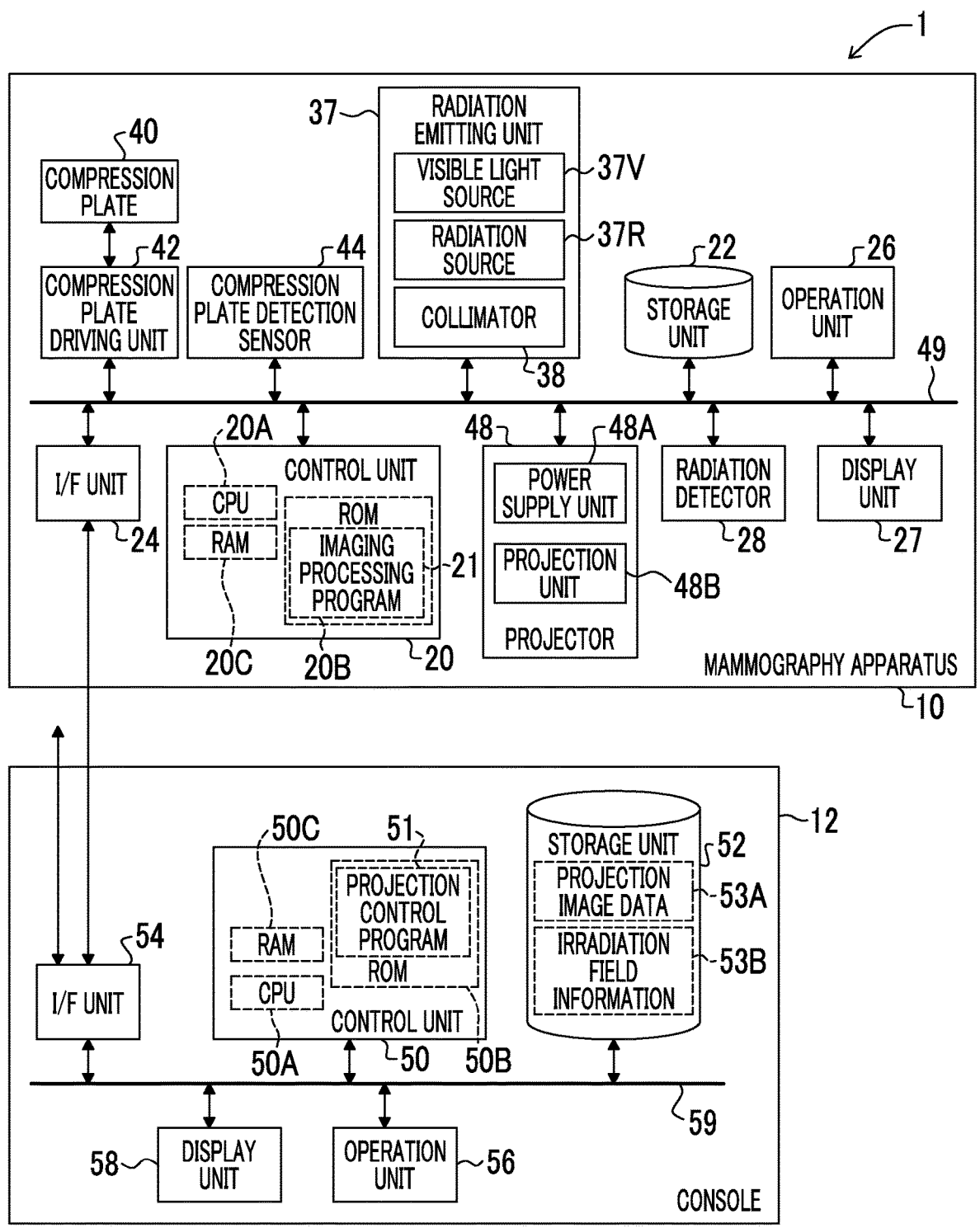
FIG. 3 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R, a visible light source 37V, and a collimator 38. As illustrated in FIG. 2A, the radiation emitting unit 37 is provided in an arm portion 32 together with the imaging table 30 and a compression unit 36. As illustrated in FIG. 2A, a face guard 39 is attachably and detachably provided at a position of the arm portion 32 which is close to the subject below the radiation emitting unit 37. The face guard 39 is a protective member for protecting the subject from the radiation R emitted from the radiation source 37R.

Further, as illustrated in FIG. 2A, the radiation emitting unit 37 further comprises a mirror 31 and a filter 33. In a case in which a tube voltage is applied to the radiation source 37R, the radiation source 37R generates the radiation R and emits the generated radiation R to the imaging table 30. The filter 33 is made of a material, such as molybdenum (Mo) or rhodium (Rh), and selectively transmits a desired wavelength component among a plurality of wavelength components included in the radiation R generated by the radiation source 37R.

In a case in which a voltage is applied to the visible light source 37V, the visible light source 37V is turned on to generate visible light V and emits the generated visible light V. For example, in the mammography apparatus 10 according to this embodiment, the visible light source 37V is provided outside an irradiation field 102 (see FIG. 2B) of the radiation R.

The mirror 31 reflects the visible light V emitted from the visible light source 37V to the imaging surface 30A of the imaging table 30 such that the irradiation field 102 which is a region irradiated with the radiation R is indicated by the visible light V. The mirror 31 transmits the radiation R emitted from the radiation source 37R.

Figure 2B:
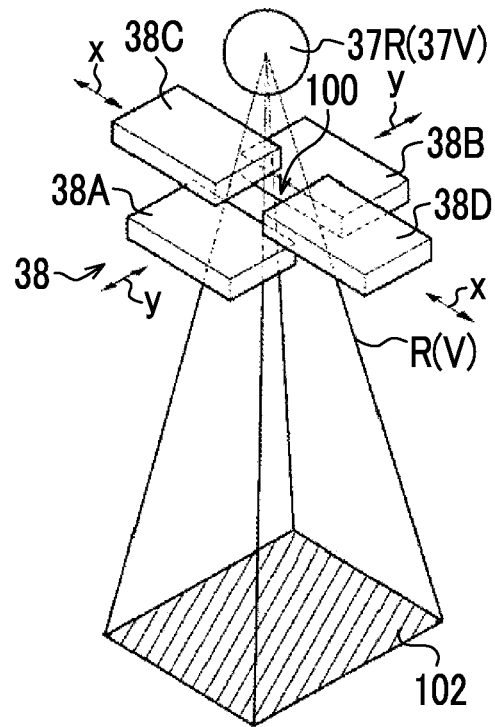
FIG. 2B is a perspective view illustrating an example of the configuration of a collimator according to the embodiment.

The collimator 38 has a function of limiting the irradiation field 102 of the radiation R and the visible light V. As illustrated in FIG. 2A, the collimator 38 is provided between the mirror 31 and the imaging table 30. FIG. 2B is a perspective view illustrating an example of the configuration of the collimator 38 according to this embodiment. As illustrated in FIG. 2B, for example, the collimator 38 according to this embodiment includes four blades 38A, 38B, 38C, and 38D. Each of the blades 38A to 38D is a plate-shaped member which has a rectangular shape in a plan view and is made of a material, such as lead or tungsten, that shields the radiation R. In the collimator 38, one side surface of the blade 38A faces one side surface of the blade 38B, and one side surface of the blade 38C faces one side surface of the blade 38D. Further, in the collimator 38, an opening portion 100 that has a rectangular shape in a plan view is formed by the side surfaces of the blades 38A to 38D which face each other.

In the collimator 38, each of the blades 38A to 38D is moved by a driving unit (not illustrated) including, for example, a motor. The blade 38A and the blade 38B can be moved in the y direction of FIG. 2B, and the blade 38C and the blade 38D can be moved in the x direction of FIG. 2B which intersects the y direction. Further, in the collimator 38 according to this embodiment, the movable range of the blades 38A to 38D is a range from a state in which the leading ends of the blades facing each other come into contact with each other, that is, a state in which the opening portion 100 is fully closed to a state in which the opening portion 100 keeps a rectangular shape in a plan view and has the maximum area. The irradiation field 102 has a shape and size (area) corresponding to the shape and size (area) of the opening portion 100. In accordance with the above, the visible light V is projected in the range of the irradiation field 102 to indicate the irradiation field 102. The mirror 31, the visible light source 37V, and the collimator 38 according to this embodiment are an example of an irradiation field projection unit according to the present disclosure. Further, in the mammography apparatus 10 according to this embodiment, the size and position of the irradiation field 102 are determined according to, for example, the type of a compression plate 40, the angle of the arm portion 32, and an instruction from the user.

In addition, as illustrated in FIG. 2A, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted by rotating the arm portion 32 to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves the compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. As illustrated in FIG. 2A, for the movement direction of the compression plate 40, the direction in which the breast is compressed, that is, the direction in which the compression plate 40 becomes closer to the imaging surface 30A is referred to as a "compression direction", and the direction in which the compression of the breast is released, that is, the direction in which the compression plate 40 becomes closer to the radiation emitting unit 37 is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2C:
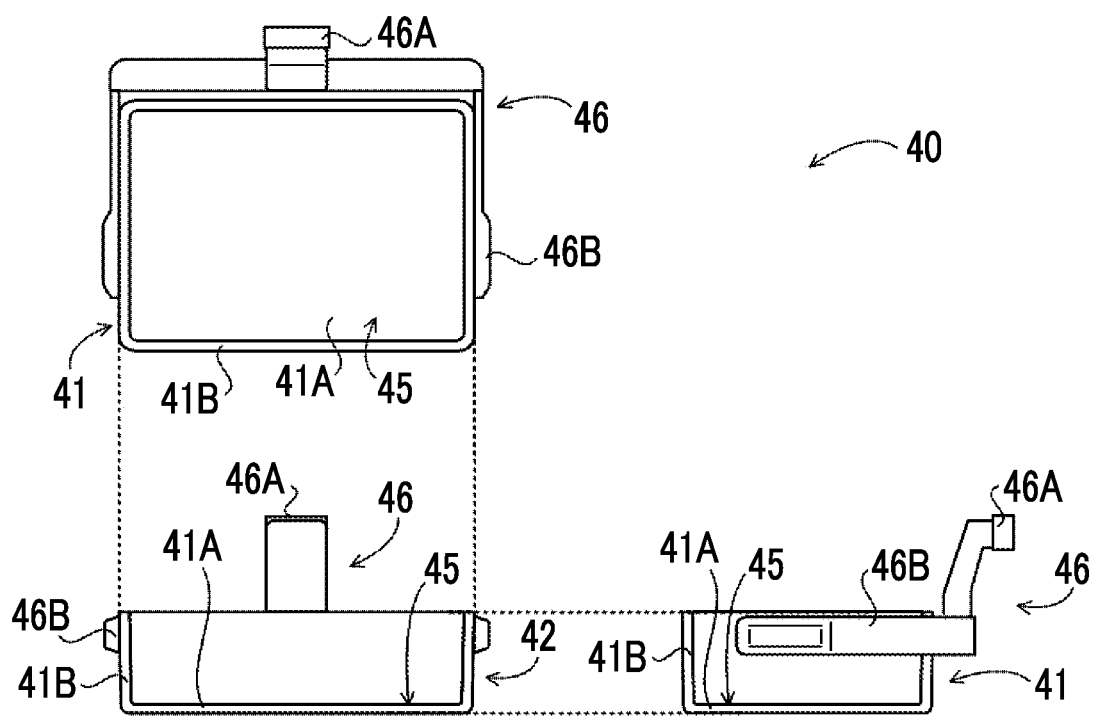
FIG. 2C is a three-view diagram illustrating an example of a compression plate according to the embodiment.

As a specific example, the compression plate 40 that can be attached to the mammography apparatus 10 according to this embodiment will be described with reference to FIG. 2C. FIG. 2C is a three-view diagram illustrating an example of the compression plate 40 according to this embodiment. The three-view diagram illustrated in FIG. 2C includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2C, the compression plate 40 according to this embodiment includes a compression portion 41 and a support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this aspect. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from the control unit 20 which will be described below. Further, the projection image P is projected from the projection unit 48B onto the projection surface 45 of the compression plate 40 in response to an instruction from the control unit 20.

Furthermore, a control unit 20, a storage unit 22, an interface (I/F) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the radiation emitting unit 37, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by a radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a projection control program 51 (which will be described below) executed by the CPU 50A are stored in the ROM 50B in advance. The RAM 50C temporarily stores various kinds of data. The CPU 50A according to this embodiment is an example of a processor according to the present disclosure. The projection control program 51 according to this embodiment is an example of a control program according to the present disclosure.

The storage unit 52 stores projection image data 53A and irradiation field information 53B which will be described in detail below. In some cases, the size of the compression portion 41 and the size of the projection surface 45 vary depending on the type of the compression plate 40. Therefore, in this embodiment, the projection image P corresponding to the type of the compression plate 40 is projected from the projector 48. For example, in this embodiment, a plurality of projection image data items indicating the projection images P corresponding to the types of the compression plate 40 are stored as the projection image data 53A in the storage unit 52 so as to be associated with the compression plate identifiers. In addition, for example, the image data of the radiographic image captured by the mammography apparatus 10 and various other kinds of information are stored in the storage unit 52. An HDD or an SSD is given as a specific example of the storage unit 52.

The operation unit 56 is used by the user to input, for example, instructions which are related to the capture of a radiographic image and which include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
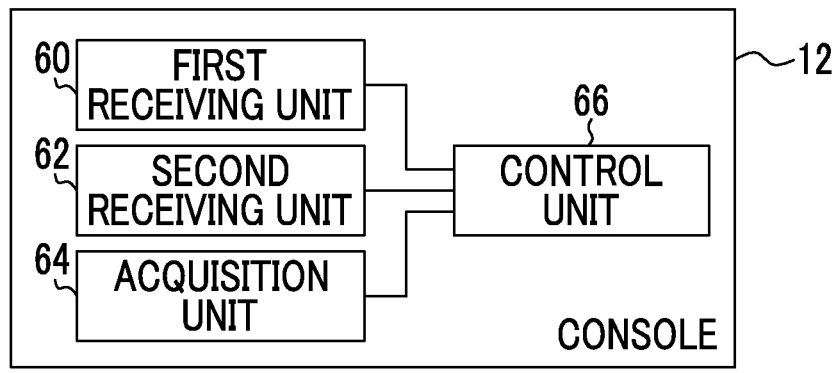
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a first receiving unit 60, a second receiving unit 62, an acquisition unit 64, and a control unit 66. For example, in the console 12 according to this embodiment, the CPU 50A of the control unit 50 executes the projection control program 51 stored in the ROM 50B to function as the first receiving unit 60, the second receiving unit 62, the acquisition unit 64, and the control unit 66.

The first receiving unit 60 has a function of receiving an instruction to start the projection of the projection image P for starting the projection of the projection image P onto the projection surface 45. For example, in this embodiment, in a case in which the user wants to start the projection of the projection image P onto the projection surface 45, the user sends an instruction to start the projection through the operation unit 26 of the mammography apparatus 10. The mammography apparatus 10 outputs a projection image projection start instruction signal through the I/F unit 24. In a case in which the projection image projection start instruction signal is input to the console 12, the first receiving unit 60 receives the instruction to start the projection of the projection image P for starting the projection of the projection image P. The first receiving unit 60 outputs projection start information of the projection image P indicating that the instruction to start the projection of the projection image P has been received to the control unit 66.

Further, the first receiving unit 60 has a function of receiving an instruction to end the projection of the projection image P for ending the projection of the projection image P onto the projection surface 45. For example, in this embodiment, in a case in which the user wants to end the projection of the projection image P onto the projection surface 45, the user sends an instruction to end the projection through the operation unit 26 of the mammography apparatus 10. The mammography apparatus 10 outputs an instruction signal for ending the projection of the projection image P through the I/F unit 24. In a case in which the instruction signal for ending the projection of the projection image P is input to the console 12, the first receiving unit 60 receives the instruction to end the projection of the projection image P for ending the projection of the projection image P. The first receiving unit 60 outputs projection end information of the projection image P indicating that the instruction to end the projection of the projection image P has been received to the control unit 66.

Further, the first receiving unit 60 has a function of receiving an instruction to start the projection of the range of the irradiation field 102 for starting the projection of the range of the irradiation field 102. For example, in this embodiment, in a case in which the user wants to start the projection of the range of the irradiation field 102, the user sends an instruction to start the projection through the operation unit 26 of the mammography apparatus 10. The mammography apparatus 10 outputs an irradiation field projection start instruction signal through the I/F unit 24. In a case in which the irradiation field projection start instruction signal is input to the console 12, the first receiving unit 60 receives the instruction to start the projection of the range of the irradiation field 102 for starting the projection of the range of the irradiation field 102. The first receiving unit 60 outputs projection start information of the irradiation field 102 indicating that the instruction to start the projection of the range of the irradiation field 102 has been received to the control unit 66.

Further, the first receiving unit 60 has a function of receiving an instruction to end the projection of the range of the irradiation field 102 for ending the projection of the range of the irradiation field 102. For example, in this embodiment, in a case in which the user wants to end the projection of the range of the irradiation field 102, the user sends an instruction to end the projection through the operation unit 26 of the mammography apparatus 10. The mammography apparatus 10 outputs an instruction signal for ending the projection of the irradiation field 102 through the I/F unit 24. In a case in which the instruction signal for ending the projection of the irradiation field 102 is input to the console 12, the first receiving unit 60 receives the instruction to end the projection of the range of the irradiation field 102 for ending the projection of the range of the irradiation field 102. The first receiving unit 60 outputs projection end information of the irradiation field 102 indicating that the instruction to end the projection of the range of the irradiation field 102 has been received to the control unit 66. In addition, hereinafter, in some cases, the projection of the range of the irradiation field 102 is simply referred to as "projection of the irradiation field 102".

The second receiving unit 62 has a function of receiving an irradiation field switching instruction for switching the size of the irradiation field 102. For example, in the mammography apparatus 10 according to this embodiment, the size of the irradiation field 102 can be switched between a state in which the size of the irradiation field 102 is smaller than the size of the projection surface 45 of the compression plate 40 and a state in which the size of the projection surface 45 is equal to the size of the irradiation field 102. The user can operate the operation unit 26 to switch the state of the size of the irradiation field 102. The second receiving unit 62 receives the user's instruction to switch the state of the size of the irradiation field 102 from the mammography apparatus 10 through the I/F unit 54. In addition, hereinafter, in some cases, the switching of the state of the size of the irradiation field 102 is simply referred to as "switching of the irradiation field 102". The second receiving unit 62 outputs switching instruction information indicating that the instruction to switch the irradiation field 102 has been received to the control unit 66.

Here, the relationship between the projection surface 45 of the compression plate 40 and the irradiation field 102 will be described in detail. As described above, in the mammography apparatus 10 according to this embodiment, the size and position of the irradiation field 102 are determined according to, for example, the type of the compression plate 40, the angle of the arm portion 32, and an instruction from the user.

Figure 5A:
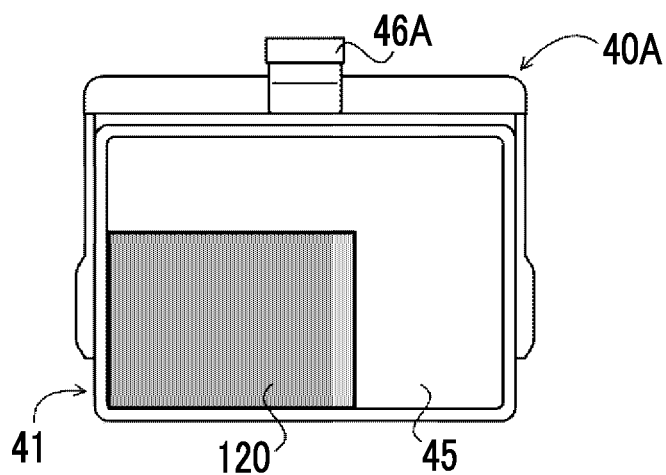
FIG. 5A is a diagram illustrating an example of the position of an irradiation field which is smaller than the size of a projection surface in a compression plate used to capture an image of a relatively large breast.
Figure 5B:
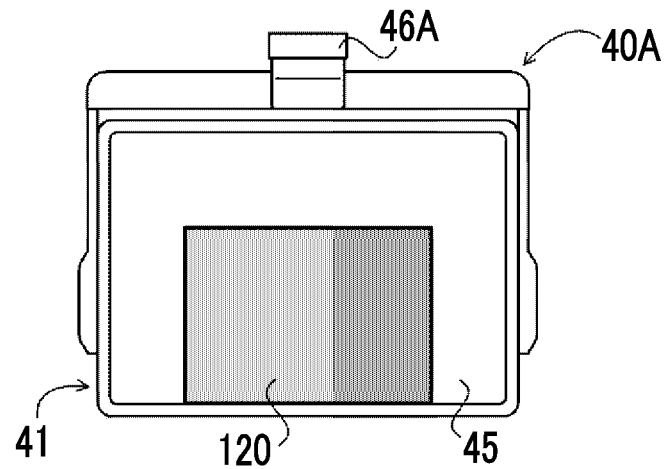
FIG. 5B is a diagram illustrating an example of the position of the irradiation field which is smaller than the size of the projection surface in the compression plate used to capture the image of the relatively large breast.
Figure 5C:
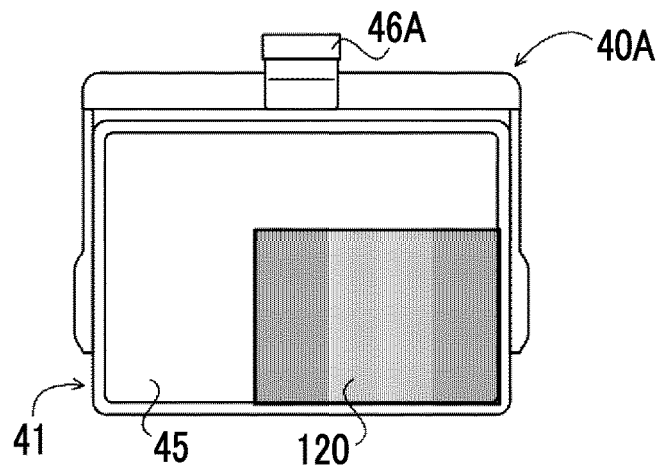
FIG. 5C is a diagram illustrating an example of the position of the irradiation field which is smaller than the size of the projection surface in the compression plate used to capture the image of the relatively large breast.

FIGS. 5A to 5C illustrate examples of the position of the irradiation field 102 which is smaller than the size of the projection surface 45 in a compression plate 40A used to capture an image of a relatively large breast. FIG. 5A illustrates the position of the irradiation field 102 with respect to the projection surface 45 of the compression plate 40A in a case in which the angle of the arm portion 32 is in the range of +36° to +146°, that is, in a case in which the MLO imaging is performed. In addition, FIG. 5B illustrates the position of the irradiation field 102 with respect to the projection surface 45 of the compression plate 40A in a case in which the angle of the arm portion 32 is equal to or less than ±36° or equal to or greater than ±146°, that is, in a case in which the arm portion 32 is inclined at an angle that is equal to or greater than that in the CC imaging or the MLO imaging. Further, FIG. 5C illustrates the position of the irradiation field 102 with respect to the projection surface 45 of the compression plate 40A in a case in which the angle of the arm portion 32 is in the range of −36° to −146°, that is, in a case in which the MLO imaging is performed. As such, in a case in which the size of the irradiation field 102 is smaller than the size of the projection surface 45 of the compression plate 40, there are three positions of the irradiation field 102 according to the angle of the arm portion 32.

Figure 5D:
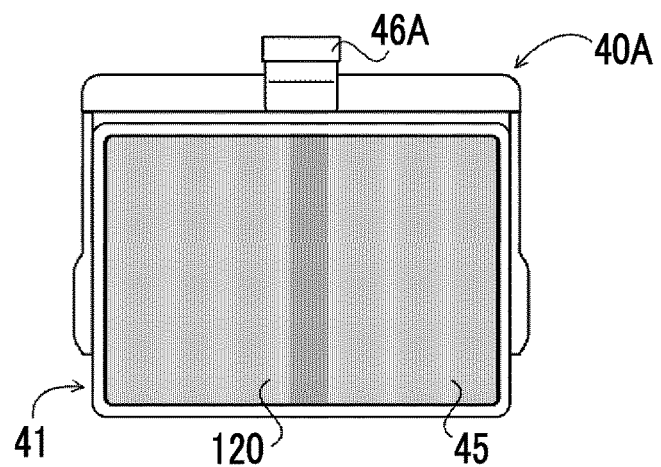
FIG. 5D is a diagram illustrating an example of the position of an irradiation field which has the same size as the projection surface in the compression plate used to capture the image of the relatively large breast.

Furthermore, FIG. 5D illustrates an example of the position of the irradiation field 102 having the same size as the projection surface 45 in the compression plate 40A. As illustrated in FIG. 5D, in this case, the entire projection surface 45 is the irradiation field 102. As described above, the states illustrated in FIGS. 5A to 5C and the state illustrated in FIG. 5D can be switched in response to the instruction from the user.

Figure 5E:
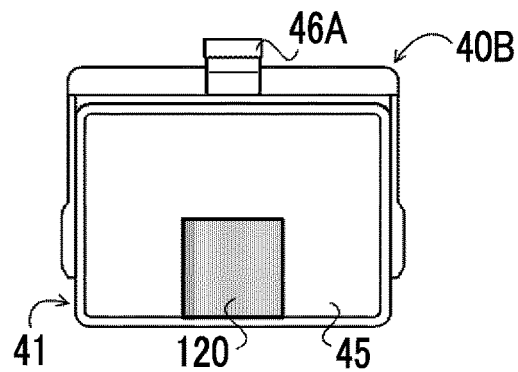
FIG. 5E is a diagram illustrating an example of the position of the irradiation field which is smaller than the size of a projection surface in a compression plate used to capture an image of a relatively small breast.

In addition, FIG. 5E illustrates an example of the position of the irradiation field 102 which is smaller than the size of the projection surface 45 in a compression plate 40B used to capture an image of a relatively large breast. The size of the projection surface 45 of the compression plate 40B is smaller than the size of the projection surface 45 of the compression plate 40A. Further, the size of the irradiation field 102 illustrated in FIG. 5E is smaller than the size of the irradiation field 102 illustrated in FIGS. 5A to 5C. As such, in this embodiment, the size of the irradiation field 102 varies depending on the type of the compression plate 40, particularly, the size of the projection surface 45.

The acquisition unit 64 has a function of acquiring the compression plate identifier of the compression plate 40 read by the compression plate detection sensor 44 from the mammography apparatus 10. Specifically, the acquisition unit 64 acquires the compression plate identifier read by the compression plate detection sensor 44 through the I/F unit 24 of the mammography apparatus 10 and the I/F unit 54 of the console 12 to acquire the compression plate identifier of the compression plate 40 attached to the compression unit 36 of the mammography apparatus 10. The acquisition unit 64 outputs the acquired compression plate identifier to the control unit 66.

In addition, the acquisition unit 64 has a function of acquiring irradiation field range information indicating the position and size of the irradiation field 102. The storage unit 52 of the console 12 according to this embodiment stores the irradiation field information 53B indicating the correspondence relationship among the compression plate identifier, angle information indicating the angle of the arm portion 32, and the irradiation field range information. For example, the irradiation field information 53B according to this embodiment includes irradiation field information $53B_1$ (see FIG. 6A) corresponding to the irradiation field range information in a case in which the size of the irradiation field 102 is smaller than the size of the projection surface 45 as illustrated in FIGS. 5A to 5C and FIG. 5E and irradiation field information $53B_2$ (see FIG. 6B) corresponding to the irradiation field range information in a case in which the size of the irradiation field 102 is equal to the size of the projection surface 45 as illustrated in FIG. 5D.

The acquisition unit 64 specifies the angle of the arm portion 32 from an imaging menu with reference to the irradiation field information $53B_1$ or the irradiation field information $53B_2$ and acquires irradiation field range information corresponding to angle information indicating the specified angle of the arm portion 32 and to the acquired compression plate identifier. In this embodiment, as illustrated in FIGS. 6A and 6B, the coordinates of the irradiation field 102 are applied as an example of the irradiation field range information. In addition, in this embodiment, the range of the irradiation field 102 has a rectangular shape as illustrated in FIG. 2B. Therefore, the size and position of the irradiation field 102 to be projected are specified by the coordinates of two vertices that face each other on a diagonal line. Further, the irradiation field range information is not limited to this embodiment and may be, for example, the size of the irradiation field 102 and the coordinates of one point of the irradiation field 102. The acquisition unit 64 outputs the acquired irradiation field range information to the control unit 66.

The control unit 66 has a function of controlling the mammography apparatus 10 such that the range of the irradiation field 102 of the radiation R is displayed by the projection image P.

As described above, in the mammography apparatus 10 according to this embodiment, in some cases, the irradiation field 102 is switched. Further, in some cases, the size or position of the irradiation field 102 varies depending on, for example, the type of the compression plate 40. Therefore, it is desirable that the user can recognize the range of the irradiation field 102.

However, the projector 48 emits projection light to project the projection image P. Further, the visible light source 37V emits visible light to project the irradiation field 102. As such, in both the projection of the projection image P by the projector 48 and the projection of the irradiation field 102 by the visible light source 37V, light is emitted to the compression plate 40 (imaging table 30). Therefore, in a case in which the projection image P and the irradiation field 102 are projected at the same time, for example, the projection image P may not be displayed due to the visible light V for projecting the irradiation field 102. Therefore, the mammography apparatus 10 according to the embodiment does not project the irradiation field 102 during the projection of the projection image P. Specifically, the control unit 66 performs control such that the visible light V is not emitted from the visible light source 37V while the projector 48 is projecting the projection image P.

However, assuming that the irradiation field 102 is not projected during the projection of the projection image P, in a case in which the irradiation field 102 is switched as described above, it is difficult for the user to recognize the position and size of the irradiation field 102 after the switching. Therefore, the control unit 66 according to this embodiment performs control to display the range of the irradiation field 102 of the radiation R using the projection image P such that the user recognizes the range of the irradiation field 102 without projecting the irradiation field 102.

Specifically, the control unit 66 according to this embodiment generates projection image data for irradiation field range display in which the size of a display image displayed on the projection surface 45 by the projection of the projection image P is equal to the size of the range of the irradiation field 102 on the projection surface 45. More specifically, the control unit 66 acquires the projection image data 53 indicating the projection image P corresponding to the compression plate identifier acquired by the acquisition unit 64 from the storage unit 52. Further, the projection image P indicated by the projection image data 53 is trimmed according to the irradiation field range information acquired by the acquisition unit 64 to generate the projection image data for irradiation field range display.

In addition, a projection image which is guide information for guiding the positioning of the breast is applied as the projection image P according to this embodiment. Specifically, a projection image projected from the projector 48 in order to display an image for guiding at least one of the shape or position of the breast compressed by the compression plate 40 on the projection surface 45 of the compression plate 40 is applied as the projection image P. For example, in this embodiment, an image indicating the skin line of the breast and the position of the nipple in a case in which the standard breast corresponding to the type of the compression plate 40 or the like is compressed to an ideal state is applied as the image for guiding at least one of the shape or position of the breast. An image indicating a skin line and the position of the nipple in this embodiment is an example of the guide information according to the present disclosure. In addition, the guide information is not limited to this embodiment as long as it is information that can guide the shape of the breast in the compressed state to the user. For example, the guide information may be any one of the skin line of the breast or the position of the nipple. Further, for example, the guide information may be the radiographic image of the breast captured in the past.

Figure 7:
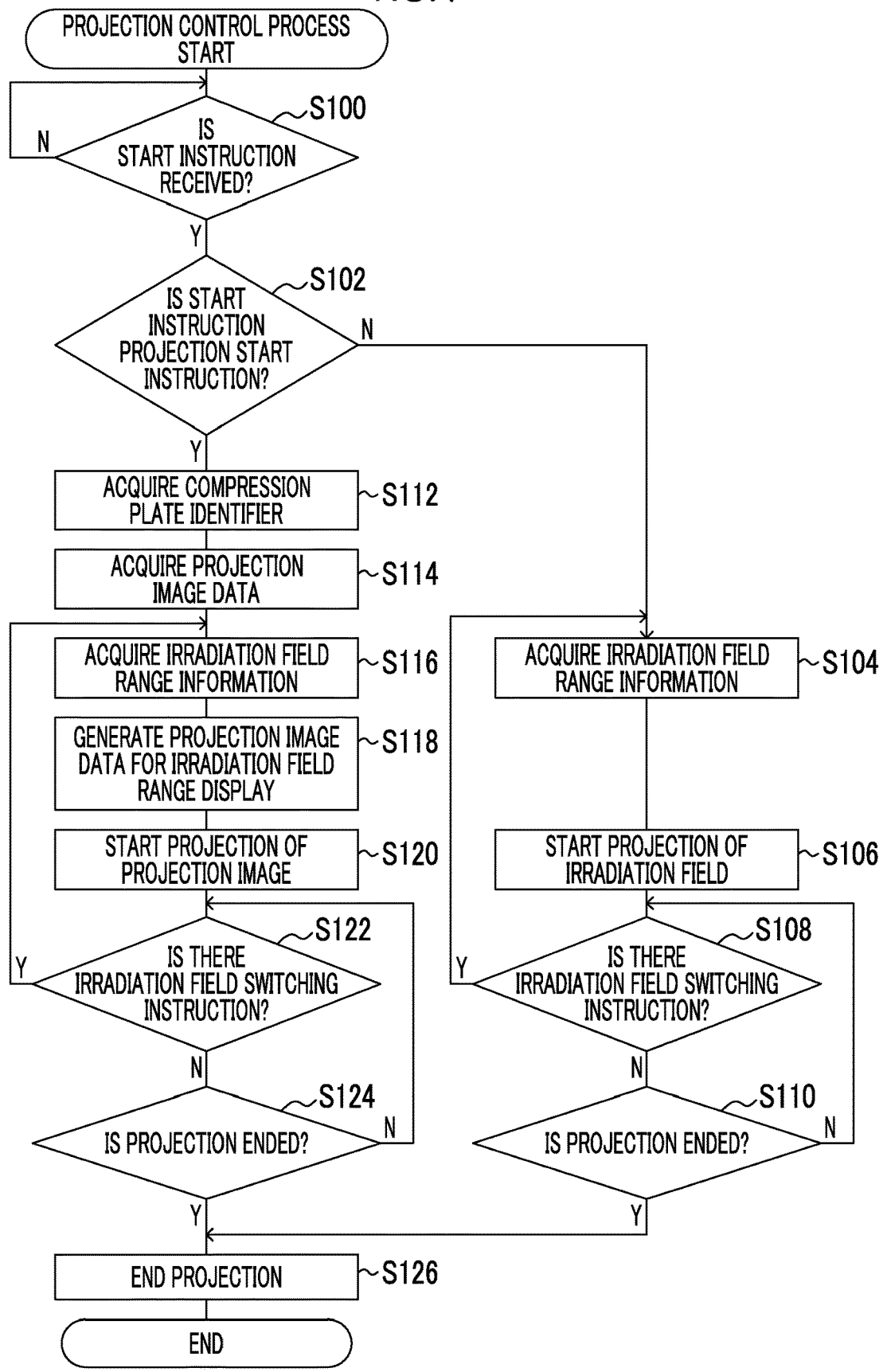
FIG. 7 is a flowchart illustrating an example of the flow of a projection control process according to the embodiment.

Next, the operation of the console 12 in the projection of the projection image P by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selection of the imaging menu, a projection control process illustrated in FIG. 7 is performed. In the console 12 according to this embodiment, for example, the CPU 50A of the control unit 50 executes the projection control program 51 stored in the ROM 50B to perform the projection control process whose example is illustrated in FIG. 7. FIG. 7 is a flowchart illustrating an example of the flow of the projection control process performed in the console 12 according to this embodiment.

In Step S100 of FIG. 7, the control unit 66 determines whether or not the first receiving unit 60 receives the instruction to start the projection of the projection image P or the instruction to start the projection of the irradiation field 102. As described above, in a case in which the user wants to start the projection of the projection image P onto the projection surface 45, the first receiving unit 60 receives the instruction to start the projection of the projection image P. In addition, in a case in which the user wants to start the projection of the irradiation field 102, the first receiving unit 60 receives the instruction to start the projection of the irradiation field 102. Therefore, in this step, it is determined whether or not the user has sent the instruction to start the projection of the projection image P or to start the projection of the irradiation field 102. The determination result in Step S100 is "No" until the first receiving unit 60 receives any one of the instruction to start the projection of the projection image P or the instruction to start the projection of the irradiation field 102. On the other hand, in a case in which the first receiving unit 60 receives the instruction to start the projection of the projection image P or the instruction to start the projection of the irradiation field 102, the determination result in Step S100 is "Yes", and the process proceeds to Step S102.

In Step S102, the control unit 66 determines whether or not the projection start instruction received by the first receiving unit 60 is the instruction to start the projection of the projection image P. In a case in which the projection start instruction received by the first receiving unit 60 is not the instruction to start the projection of the projection image P, that is, in a case in which the first receiving unit 60 receives the instruction to start the projection of the irradiation field 102, the determination result in Step S102 is "No", and the process proceeds to Step S104.

In Step S104, as described above, the acquisition unit 64 acquires the irradiation field information with reference to the irradiation field information 53B in the storage unit 52.

Then, in Step S106, the control unit 66 performs control to start the projection of the irradiation field 102. Specifically, the control unit 66 outputs the irradiation field range information acquired in Step S104 to the mammography apparatus 10 through the I/F unit 54. The control unit 20 of the mammography apparatus 10 performs control such that the opening portion 100 of the collimator 38 of the mammography apparatus 10 has a size corresponding to the irradiation field range information and the visible light V is emitted from the visible light source 37V.

Then, in Step S108, the control unit 66 determines whether or not the switching of the irradiation field 102 is instructed. In a case in which the second receiving unit 62 receives the switching instruction, the determination result in Step S108 is "Yes", and the process returns to Step S104. Then, the processes in Steps S104 and S106 are repeated according to the irradiation field 102 after switching. In a case in which the second receiving unit 62 does not receive the switching instruction, the determination result in Step S108 is "No", and the process proceeds to Step S110.

In Step S110, the control unit 66 determines whether or not to end the projection of the irradiation field 102.

As described above, in a case in which the first receiving unit 60 does not receive the instruction to end the projection of the irradiation field 102, the determination result in Step S110 is "No", and the process returns to Step S108. On the other hand, in a case in which the first receiving unit 60 receives the instruction to end the projection of the irradiation field 102, the determination result in Step S110 is "Yes", and the process proceeds to Step S126.

On the other hand, in a case in which the projection start instruction received by the first receiving unit 60 is the instruction to start the projection of the irradiation field 102, the determination result in Step S102 is "Yes", and the process proceeds to Step S112. In Step S112, the acquisition unit 64 acquires the compression plate identifier from the mammography apparatus 10 as described above.

Then, in Step S114, the control unit 66 acquires the projection image data 53A corresponding to the compression plate identifier acquired in Step S112 from the storage unit 52 as described above.

Then, in Step S116, the acquisition unit 64 acquires the irradiation field range information corresponding to the compression plate identifier acquired in Step S112 and to the angle of the arm portion 32 with reference to the irradiation field information $53B_1$ or the irradiation field information $53B_2$ corresponding to the setting of switching, among the irradiation field information 53B stored in the storage unit 52 as described above.

Then, in Step S118, the control unit 66 trims the projection image P corresponding to the projection image data acquired in Step S114 on the basis of the irradiation field range information acquired in Step S116 to generate projection image data for irradiation field range display as described above.

Then, in Step S120, the control unit 66 performs control to start the projection of the projection image P. Specifically, the control unit 66 outputs the projection image data for irradiation field range display acquired in Step S118 to the mammography apparatus 10 through the I/F unit 54. In the mammography apparatus 10, in a case in which the projection image data for irradiation field range display is input, the control unit 20 performs control such that the projection unit 48B of the projector 48 projects the projection image P corresponding to the projection image data for irradiation field range display. An image indicating the skin line of the breast and the position of the nipple is displayed in the range of the irradiation field 102 on the projection surface 45 of the compression plate 40 attached to the compression unit 36 of the mammography apparatus 10 according to the projection image P by this control.

FIGS. 8A to 8D illustrate examples of a skin line 70 and a position 72 of the nipple which are displayed on the projection surface 45 of the compression plate 40 according to the projection image P projected by the projection image data for displaying the irradiation field 102 corresponding to each of FIGS. 5A to 5D. In the examples illustrated in FIGS. 8A to 8D, the skin line 70 is displayed inside the range of the irradiation field 102 and is not displayed outside the irradiation field 102. Therefore, the user can recognize the range of the irradiation field 102 according to whether or not the skin line 70 is displayed. The user compresses the breast of the subject positioned with reference to the displayed skin line 70 and the displayed position 72 of the nipple with the compression plate 40.

Then, in Step S122, the control unit 66 determines whether or not to switch the irradiation field 102. In this embodiment, in a case in which the angle of the arm portion 32 is changed or in a case in which the second receiving unit 62 receives the instruction to switch the irradiation field 102, the irradiation field 102 is switched. Therefore, the control unit 66 determines whether or not to switch the irradiation field 102 according to the angle of the arm portion 32 and whether or not the second receiving unit 62 receives the irradiation field switching instruction. In a case in which the irradiation field 102 is switched, the determination result in Step S122 is "Yes", and the process returns to Step S116. Then, the processes in Steps S116 to S120 are repeated.

That is, in a case in which the size of the irradiation field 102 is switched to be larger or smaller than the size of the projection surface 45 of the compression plate 40 in response to the irradiation field switching instruction, the irradiation field range information corresponding to the compression plate identifier acquired in Step S112 and the angle of the arm portion 32 is acquired with reference to the corresponding irradiation field information 53B$_1$ or irradiation field information 53B$_2$ after the switching. Then, the projection image P corresponding to the projection image data acquired in Step S114 is trimmed on the basis of the acquired irradiation field range information to generate projection image data for irradiation field range display. Then, the projection of the projection image P corresponding to the generated projection image data is started.

As such, in this embodiment, in a case in which the size of the range of the irradiation field 102 is changed in response to the irradiation field switching instruction, the size of the display image displayed by the projection image P is changed according to the changed size.

Figure 8A:
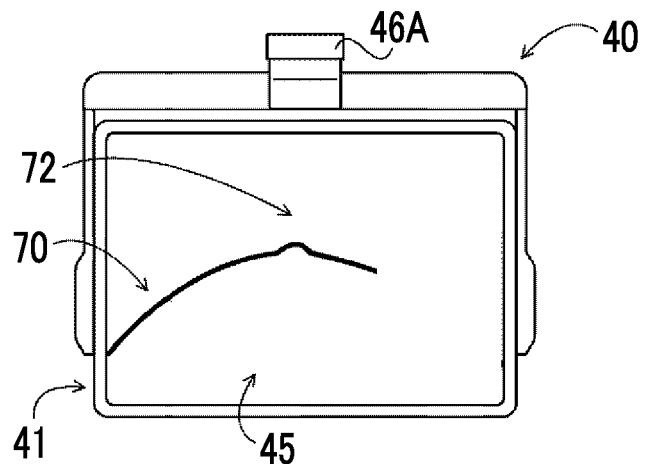
FIG. 8A is a diagram illustrating an example of a display state that corresponds to a projection image projected by projection image data for irradiation field display corresponding to FIG. 5A.
Figure 8B:
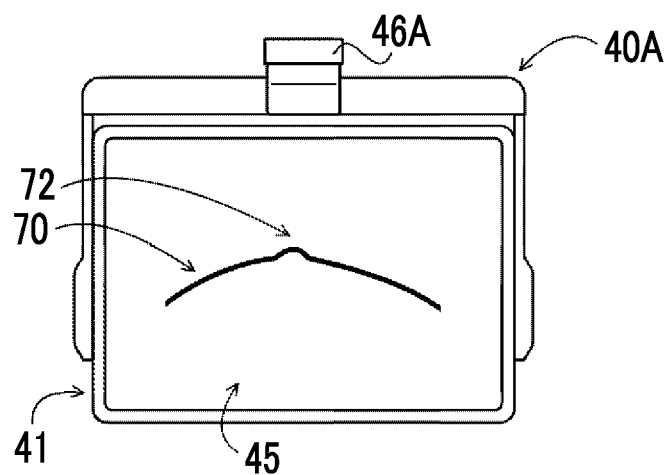
FIG. 8B is a diagram illustrating an example of a display state that corresponds to a projection image projected by projection image data for irradiation field display corresponding to FIG. 5B.
Figure 8C:
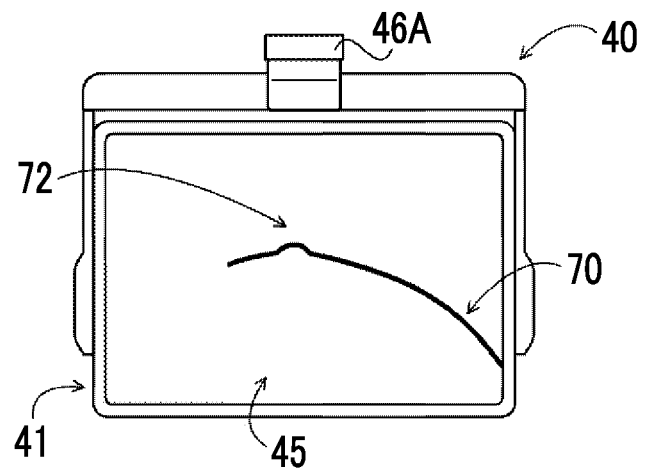
FIG. 8C is a diagram illustrating an example of a display state that corresponds to a projection image projected by projection image data for irradiation field display corresponding to FIG. 5C.
Figure 8D:
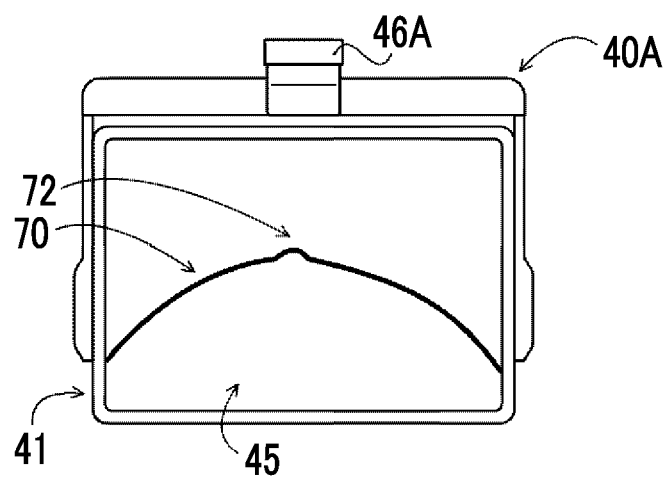
FIG. 8D is a diagram illustrating an example of a display state that corresponds to a projection image projected by projection image data for irradiation field display corresponding to FIG. 5D.

For example, in a case in which the range of the irradiation field 102 is switched from the state illustrated in FIG. 5A to the state illustrated in FIG. 5B by the rotation of the arm portion 32, the display of the skin line 70 and the position 72 of the nipple on the projection surface 45 of the compression plate 40 by the projection image P is switched from the state illustrated in FIG. 8A to the state illustrated in FIG. 8B. Further, for example, in a case in which the range of the irradiation field 102 is switched from the state illustrated in FIG. 5B to the state illustrated in FIG. 5D by the instruction to switch the irradiation field 102 from the user, the size of the display image displayed on the projection surface 45 by the projection image P is different from the size of the irradiation field 102. Therefore, the display of the skin line 70 and the position 72 of the nipple on the projection surface 45 of the compression plate 40 by the projection image P is switched from the state illustrated in FIG. 8B to the state illustrated in FIG. 8D.

On the other hand, in a case in which the irradiation field 102 is not switched, the determination result in Step S122 is "No", and the process proceeds to Step S124. In Step S124, the control unit 66 determines whether or not to end the projection of the projection image P. As described above, in a case in which the first receiving unit 60 does not receive the instruction to end the projection of the projection image P, the determination result in Step S124 is "No", and the process returns to Step S122. On the other hand, in a case in which the first receiving unit 60 receives the instruction to end the projection of the projection image P, the determination result in Step S124 is "Yes", and the process proceeds to Step S126.

In Step S126, the control unit 66 ends the projection. Specifically, in a case in which the projection image P has been projected, the control unit 66 outputs the projection end signal of the projection image P for ending the projection of the projection image P to the mammography apparatus 10 through the I/F unit 54. In the mammography apparatus 10, in a case in which the projection end signal of the projection image P is input, the control unit 20 ends the projection of the projection image P by the projection unit 48B of the projector 48. Specifically, the emission of the projection light for projecting the projection image P is stopped. In addition, in a case in which the projection of the projection image P is ended, the supply of power to the power supply unit 48A is cut off to turn off the power supply unit 48A.

Further, in a case in which the irradiation field 102 has been projected, the control unit 66 outputs the projection end signal of the irradiation field 102 for ending the projection of the irradiation field 102 to the mammography apparatus 10 through the I/F unit 54. In the mammography apparatus 10, in a case in which the projection end signal of the irradiation field 102 is input, the control unit 20 turns off the visible light source 37V to stop the emission of the visible light V, thereby ending the projection of the irradiation field 102.

In a case in which the process in Step S126 ends in this way, the projection control process illustrated in FIG. 7 ends.

As such, the console 12 according to this embodiment makes the display size of the projection image P equal to the range of the irradiation field 102 of the radiation R. Therefore, according to the console 12 of this embodiment, the skin line 70 and the position 72 of the nipple are displayed within the range of the irradiation field 102. The skin line 70 and the position 72 of the nipple are not displayed outside the range of the irradiation field 102. Therefore, according to the console 12 of this embodiment, the user can recognize the range of the irradiation field 102 from the image of the skin line 70 and the position 72 of the nipple without projecting the irradiation field 102.

Figure 9:
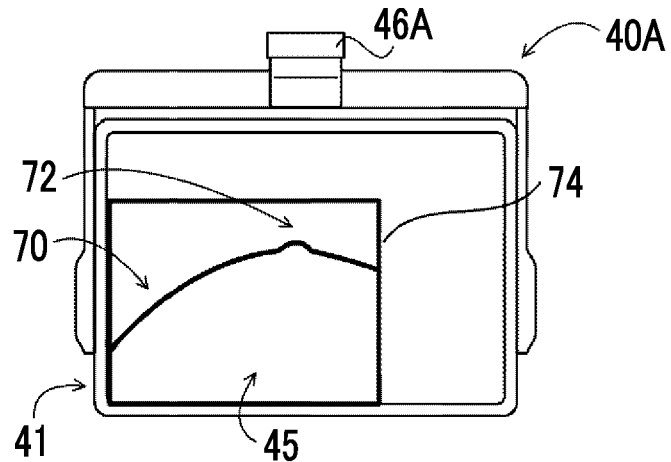
FIG. 9 is a diagram illustrating an example of a state in which an irradiation field boundary line indicating a range of the irradiation field is displayed by the projection image.

In addition, in the above-described embodiment, the aspect in which the image indicating the skin line 70 and the position 72 of the nipple is displayed by the projection image P has been described. However, the image displayed by the projection image P is not limited thereto. For example, as illustrated in FIG. 9, an irradiation field boundary line 74 indicating the range of the irradiation field 102 may be displayed by the projection image P. In this case, the irradiation field boundary line 74 enables the user to more clearly recognize the range of the irradiation field 102. Further, the irradiation field boundary line 74 is not limited to the aspect in which the entire boundary line of the irradiation field 102 is represented by lines. For example, a portion of the boundary line may be represented by lines, or each of four corners of the rectangular irradiation field 102 may be represented by a mark.

Furthermore, in the above-described embodiment, the aspect in which the display size of the projection image P is equal to the range of the irradiation field 102 of the radiation R. However, the display size of the projection image P may be constant regardless of the range of the irradiation field 102. In this case, only the image of the skin line 70 and the position 72 of the nipple included in the projection image P may be trimmed according to the range of the irradiation field 102.

Moreover, for example, an image in which at least one of brightness, saturation, or luminance is different between a region in the range of the irradiation field 102 and a region outside the range of the irradiation field 102 may be applied as the image displayed by the projection image P. In this case, the difference in the brightness, saturation, and luminance of the displayed image enables the user to recognize the range of the irradiation field 102.

In addition, in the above-described embodiment, the aspect in which the image of the skin line 70 and the position 72 of the nipple is not displayed outside the range of the irradiation field 102, that is, the aspect in which the guide information is not displayed outside the range of the irradiation field 102 such that the guide information is different inside and outside the range of the irradiation field 102 has been described. However, the present disclosure is not limited to this aspect. For example, the color or type (a solid line, a dotted line, or the like) of the displayed line may be different inside and outside the range of the irradiation field 102. In other words, information may be displayed in different ways inside and outside the range of the irradiation field 102 such that the guide information is different inside and outside the range of the irradiation field 102. In this case, the difference in how the information is displayed depending on the color and type of the displayed line enables the user to recognize the range of the irradiation field 102.

Further, the projection image P is not limited to the projection image for displaying the image for guiding at least one of the shape or position of the breast on the projection surface 45 of the compression plate 40 and may be a projection image for displaying imaging information. Furthermore, examples of the imaging information include information related to the current imaging, such as an imaging date and time or a radiographer, information related to the past imaging, such as compression pressure in the past imaging, and information related to the subject, such as the name of the subject. Moreover, the image indicating the imaging information may be an image indicating characters or numbers.

Figure 10:
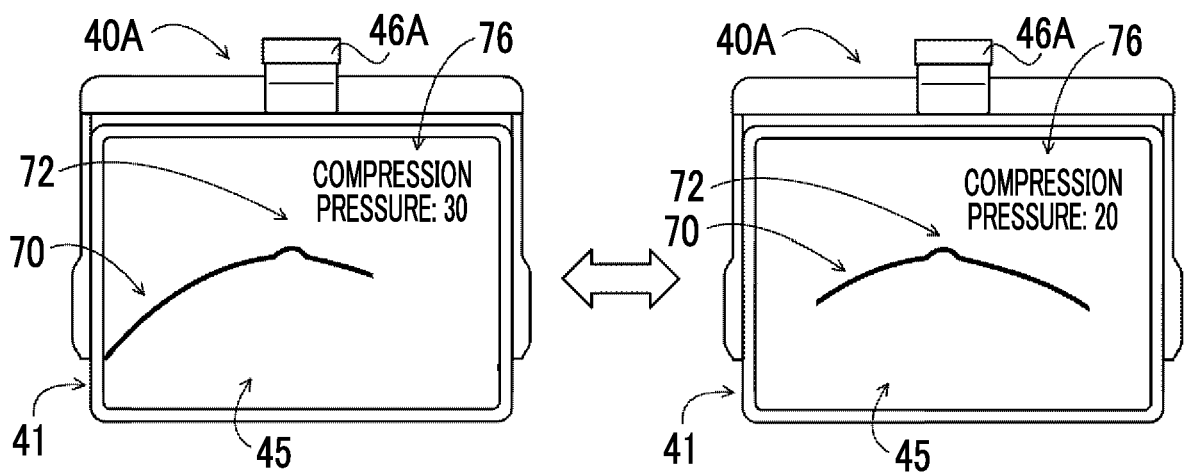
FIG. 10 is a diagram illustrating an example of a change in the state of display on the projection surface of the compression plate by the projection image in a case in which the range of the irradiation field is switched.

As such, in a case in which the imaging information is displayed by the projection image P and the position where the imaging information is displayed changes as the range of the irradiation field 102 is switched, it may be difficult for the user to see the imaging information, or the user may be confused. Therefore, even in a case in which the range in which the skin line 70 displayed by the projection image P is displayed is changed by the switching of the range of the irradiation field 102 as in the above-described embodiment, the position where the imaging information is displayed may not change. An example of this case is illustrated in FIG. 10. FIG. 10 illustrates a state in which the skin line 70, the position 72 of the nipple, and imaging information 76 are displayed on the projection surface 45 of the compression plate 40 by the projection image P in a case in which the range of the irradiation field 102 is switched between the state illustrated in FIG. 5A and the state illustrated in FIG. 5B. In addition, characters indicating compression pressure are applied as an example of the imaging information 76. Further, at least one of the current compression pressure of the compression plate 40 against the breast or the compression pressure in a case in which compression was completed in the past imaging is given as an example of the "compression pressure". In the example illustrated in FIG. 10, even in a case in which the range in which the skin line 70 is displayed changes as the range of the irradiation field 102 is switched, the position where the imaging information 76 is displayed does not change. Since the imaging information 76 is at the same position with respect to the projection surface 45 regardless of the position of the irradiation field 102, the user can easily see the imaging information 76. In particular, in a case in which the imaging information 76 is characters or numbers, it is displayed at the same position, which makes it possible for the user to easily see the imaging information 76.

Figure 11:
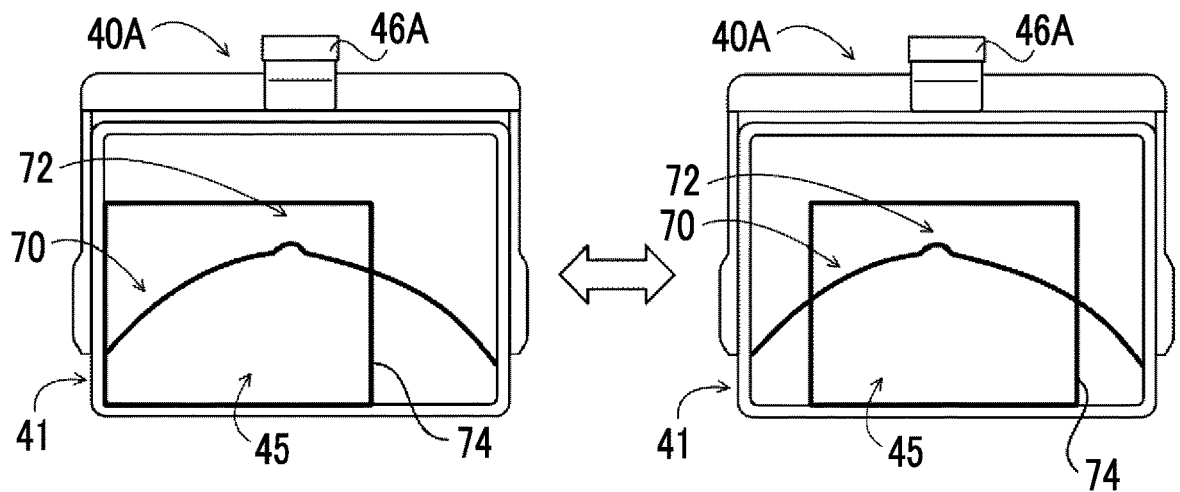
FIG. 11 is a diagram illustrating an example of an aspect in which only an image indicating the range of the irradiation field displayed by the projection image is changed in a case in which the irradiation field is switched.

Further, even in a case in which the irradiation field 102 is switched, the display state of the skin line 70, the position 72 of the nipple, the imaging information 76, and the like may not change, and only the image indicating the range of the irradiation field 102 may change as the irradiation field 102 is switched. An example of this case is illustrated in FIG. 11. FIG. 11 illustrates a state in which the skin line 70, the position 72 of the nipple, and the irradiation field boundary line 74 are displayed on the projection surface 45 of the compression plate 40 by the projection image P in a case in which the range of the irradiation field 102 is switched between the state illustrated in FIG. 5A and the state illustrated in FIG. 5B. In the example illustrated in FIG. 11, as the range of the irradiation field 102 is switched, only the irradiation field boundary line 74 changes, and the display state of the skin line 70 and the position 72 of the nipple does not change. As such, since the display state of the skin line 70 and the position 72 of the nipple does not change, the skin line 70 of the entire breast remains displayed. Therefore, it is easy for the user to appropriately compress the breast. In addition, in this case, for example, the following aspect may be used: a plurality of projection image data items 53 associated with the compression plate identifier and the irradiation field range information are stored in the storage unit 52, and the control unit 66 acquires the projection image data 53 corresponding to the compression plate identifier and the irradiation field range information acquired by the acquisition unit 64 from the storage unit 52.

Figure 12:
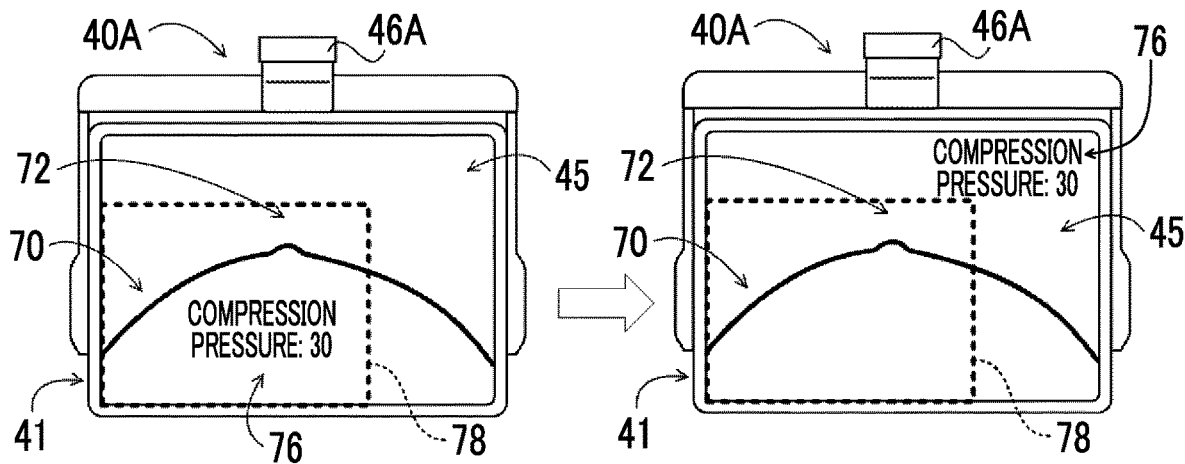
FIG. 12 is a diagram illustrating an example of a change in the state of display by the projection image before and after the irradiation field is projected during the projection of the projection image.

Further, in the above-described embodiment, the aspect in which the first receiving unit 60 does not receive the instruction to start the projection of the irradiation field 102 during the projection of the projection image P. However, the first receiving unit 60 may receive the instruction to start the projection of the irradiation field 102 during the projection of the projection image P. In this case, it is difficult or impossible for the user to see the projection image P in the region in which the visible light V is emitted on the other surface onto which the irradiation field 102 is projected. Therefore, in a case in which the irradiation field 102 is also projected during the projection of the projection image P, the control unit 66 may perform control to project the projection image P for displaying information outside a region inside the irradiation field 102. For example, the control unit 66 may perform control such that the position where the imaging information 76 is displayed is outside the range of the irradiation field 102 as illustrated in FIG. 12 in a case in which the irradiation field 102 is projected during the projection of the projection image P. FIG. 12 illustrates an example of a change in the display state of the skin line 70, the position 72 of the nipple, and the imaging information 76 before the irradiation field 102 is projected and after the irradiation field 102 is projected during the projection of the projection image P. In addition, in FIG. 12, for convenience, the range of the irradiation field 102 is represented by a dotted line. However, in practice, the dotted line indicating the irradiation field 102 is not displayed. In the example illustrated in FIG. 12, the display state of the skin line 70 and the position 72 of the nipple does not change regardless of whether or not the irradiation field 102 is projected. On the other hand, the display position of the imaging information 76 is changed to the outside of the region of the irradiation field 102 in a case in which the irradiation field 102 is projected as described above. As such, in a case in which the irradiation field 102 is projected, the imaging information 76 is displayed outside the region in which the visible light V is emitted. Therefore, it is possible to see the imaging information 76 regardless of the visible light V.

In addition, a specific method for displaying the imaging information 76 outside the region of the irradiation field 102 is not limited. For example, the storage unit 52 may store the projection image data 53 indicating the projection image P for displaying information outside the range of the irradiation field 102. In this case, the control unit 66 may acquire, from the storage unit 52, the projection image data 53 for displaying information outside the range of the irradiation field 102 indicated by the irradiation field range information acquired by the acquisition unit 64 and may switch the projection image data 53 of the projection image P to be displayed. Further, for example, instead of switching the projection image P to be projected, the emission direction or position of the projection light by the projector 48 may be adjusted to display information outside the irradiation field 102 using the projection image P.

In addition, the position outside the region of the irradiation field 102 is not particularly limited and may not be within the projection surface 45. For example, the wall portion 41B of the compression plate 40 may be applied as the position outside the region of the irradiation field 102.

As described above, the console 12 according to the above-described embodiment comprises the CPU 50A which corresponds to at least one processor. The CPU 50A controls the projector 48 which projects the projection image P onto the projection surface 45 of the compression plate 40 of the mammography apparatus 10 that irradiates the breast compressed by the compression plate 40 with the radiation R to capture a radiographic image such that the range of the irradiation field 102 of the radiation R is displayed by the projection image P.

As such, according to the console 12 of the above-described embodiment, the projection image P is projected to display the range of the irradiation field 102. Therefore, the console 12 according to this embodiment enables the user to recognize the range of the irradiation field 102 without projecting the irradiation field 102.

Further, in the above-described embodiment, the aspect in which both the size of the projection image P and the size of the irradiation field 102 are equal to or less than the size of the projection surface 45 has been described. However, the size of the projection image P and the size of the irradiation field 102 may be equal to or greater than the size of the projection surface 45 of the compression plate 40. That is, at least one of the projection image P or the irradiation field 102 may be projected onto the imaging surface 30A of the imaging table 30.

Further, in the above-described embodiment, the aspect in which the projection of each of the projection image P and the irradiation field 102 is started in response to the instruction from the user has been described. However, the timing when the projection of each of the projection image P and the irradiation field 102 is started is not limited to this aspect. For example, in a case in which the compression plate 40 is moved in the compression direction, the projection of the projection image P may be automatically started.

In addition, in the above-described embodiment, the aspect in which the projection of each of the projection image P and the irradiation field 102 ends in a case in which the user inputs the instruction to end the projection has been described. However, the timing when the projection of each of the projection image P and the irradiation field 102 ends is not limited to this aspect. For example, the projection may end at the timing when the emission of the radiation R by the radiation source 37R ends.

Further, in the above-described embodiment, the image indicating the skin line of the breast and the position of the nipple in a case in which the standard breast is compressed into an ideal state is applied as the projection image P. However, the projection image P is not limited to this aspect. For example, the projection image P may be the radiographic image of the breast of the same subject captured in the past, an image indicating a skin line generated from the radiographic image captured in the past, or the like. In addition, a method for generating the image indicating the skin line is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line.

Further, in a case in which the image indicating the skin line is generated from the radiographic image captured in the past and is projected onto the projection surface 45 and the skin line image generated from the radiographic image captured in the past is projected as the projection image P without any change, the size of the projection image P may be different from the size of the projection surface 45.

In a case in which the radiographic image captured in the past is larger than the projection surface 45, the control unit 66 may generate an image indicating the skin line based on the shape of the breast indicated by a partial region of the radiographic image which corresponds to the size of the projection surface 45. In other words, the control unit 66 may cut a partial region corresponding to the size of the projection surface 45 in the radiographic image captured in the past and may generate the image indicating the skin line on the basis of the cut image. In addition, in many cases, the mammography apparatus 10 captures an image including a chest wall side. Therefore, the region to be cut is preferably a partial region on the chest wall side. Further, it is preferable that the region to be cut is a partial region including the center of the shape of the breast included in the radiographic image in the left-right direction.

Furthermore, in a case in which the radiographic image captured in the past is smaller than the projection surface 45, the control unit 66 may generate an image indicating the skin line in which the shape of the breast outside the radiographic image has been complemented on the basis of the shape of the breast indicated by the radiographic image. A known image complementing method can be applied as the complementing method. For example, the control unit 66 may complement an extension line on the basis of the curvature of the skin line of a portion generated on the basis of the radiographic image captured in the past. Further, for example, the control unit 66 may complement a tangent line of the skin line of the portion generated on the basis of the radiographic image as the extension line.

Further, in a case in which the size of the radiographic image captured in the past and the size of the projection surface 45 are not matched with each other, the control unit 66 may generate the image indicating the skin line based on the shape of the breast indicated by an image obtained by enlarging or reducing the radiographic image captured in the past according to the size of the projection surface 45. For example, an enlargement and reduction ratio may be predetermined for each combination of the size of the radiographic image and the size of the projection surface 45.

In addition, the configuration for projecting the projection image P in the mammography apparatus 10 described in the above-described embodiment is not limited and is not limited to the aspect using the projector 48. Further, in a case in which the projector 48 is applied, the configuration of the projector 48 is not limited. For example, in the above-described embodiment, the aspect in which the projection image P projected from the projector 48 is directly projected onto the projection surface 45 has been described. However, the projection image P may be reflected from a mirror or the like to be projected onto the projection surface 45. In this case, the direction in which the projection image P is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P onto the projection surface 45. Specifically, in a case in which the projection of the projection image P is started, control is performed such that the shutter is opened to transmit the projection light. On the other hand, in a case in which the projection of the projection image P is ended, control is performed such that the shutter is closed to block the projection light. In addition, in a case in which the shutter that blocks the projection light is provided in this way, an opening portion of the shutter may be provided to be the same as the opening portion 100 of the collimator 38 of the mammography apparatus 10 such that the display size of the projection image P is equal to the size of the irradiation field 102.

Further, in the above-described embodiment, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the first receiving unit 60, the second receiving unit 62, the acquisition unit 64, and the control unit 66.

Further, in the above-described embodiment, for example, the following various processors can be used as the hardware structure of processing units performing various processes such as the first receiving unit 60, the second receiving unit 62, the acquisition unit 64, and the control unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the projection control program 51 is stored (installed) in the ROM 50B in advance has been described. However, the present disclosure is not limited thereto. The projection control program 51 may be recorded on a recording medium, such as a compact disc read only memory (CD-ROM), a digital versatile disc read only memory (DVD-ROM), or a universal serial bus (USB) memory, and then provided. In addition, the projection control program 51 may be downloaded from an external device through a network.

What is claimed is:

1. A control device comprising:
   at least one processor,
   wherein the processor is configured to:
   acquire a compression plate identifier that identifies a type of a compression member attached to a mammography apparatus and an angle of an arm portion of the mammography apparatus, the mammography apparatus being configured to irradiate a breast compressed by the compression member with radiation to capture a radiographic image;

acquire irradiation field information indicating a size of a range of an irradiation field of the radiation of the mammography apparatus, based on the compression plate identifier and the angle of an arm portion, the irradiation field information comprising information expressing a relationship of the compression plate identifier, the angle of the arm portion and the size of the range of the irradiation field; and control an image projection unit that projects a projection image onto a projection surface of the compression member such that a range of an irradiation field of the radiation is displayed by the projection image, in a case in which a size of a display image displayed on the projection surface by the projection image is different from the size of the range of the irradiation field indicated by the irradiation field information, wherein a display image displayed on the projection surface due to the projection of the projection image is an image larger than the range of the irradiation field on the projection surface of the compression member.

2. The control device according to claim 1, wherein the processor performs control to display the range of the irradiation field such that a size of a display image displayed by the projection of the projection image is equal to a size of the range of the irradiation field.

3. The control device according to claim 1, wherein the processor acquires irradiation field information indicating a size of the range of the irradiation field of the radiation and performs control to change a size of a display image displayed by the projection of the projection image depending on the size of the range of the irradiation field in a case in which the size of the range of the irradiation field indicated by the irradiation field information is changed.

4. The control device according to claim 1, wherein the processor performs control such that a projection image including irradiation field information indicating the range of the irradiation field is projected to display the range of the irradiation field.

5. The control device according to claim 1, wherein the projection image includes guide information for guiding a shape of the breast in a compressed state, and
the processor performs control such that the guide information is different inside and outside the range of the irradiation field to display the range of the irradiation field.

6. The control device according to claim 5, wherein the processor performs control such that the guide information is not displayed outside the range of the irradiation field for the difference.

7. The control device according to claim 1, wherein the projection image includes imaging information, and
the processor performs control to display the imaging information at the same position regardless of the range of the irradiation field.

8. The control device according to claim 7, wherein the imaging information includes at least information indicating a compression pressure of the compression member against the breast.

9. The control device according to claim 1, wherein the processor controls an irradiation field projection unit which projects visible light within the range of the irradiation field to indicate the range of the irradiation field such that the range of the irradiation field is displayed in a case in which the image projection unit does not project the projection image.

10. The control device according to claim 1, wherein the projection image includes imaging information, and
in a case in which an instruction for an irradiation field projection unit, which projects visible light within the range of the irradiation field to indicate the range of the irradiation field, to display the range of the irradiation field is received during the projection of the projection image by the image projection unit, the processor performs control to switch to a projection image for displaying the imaging information outside the range of the irradiation field or control to switch a projection position of the projection image to a state in which the imaging information is displayed outside the range of the irradiation field.

11. The control device according to claim 10, wherein the projection image further includes guide information for guiding a shape of the breast in a compressed state, and
the processor performs control that a position where the guide information is displayed remains the same.

12. A control method comprising:
acquiring a compression plate identifier that identifies a type of a compression member attached to a mammography apparatus and an angle of an arm portion of the mammography apparatus, the mammography apparatus being configured to irradiate a breast compressed by the compression member with radiation to capture a radiographic image;

acquiring irradiation field information indicating a size of a range of an irradiation field of the radiation of the mammography apparatus, based on the compression plate identifier and the angle of an arm portion, the irradiation field information comprising information expressing a relationship of the compression plate identifier, the angle of the arm portion and the size of the range of the irradiation field; and controlling an image projection unit that projects a projection image onto a projection surface of the compression member such that a range of an irradiation field of the radiation is displayed by the projection image, in a case in which a size of a display image displayed on the projection surface by the projection image is different from the size of the range of the irradiation field indicated by the irradiation field information, wherein a display image displayed on the projection surface due to the projection of the projection image is an image larger than the range of the irradiation field on the projection surface of the compression member.

13. A non-transitory computer-readable storage medium storing a control program that causes a computer to perform a process of:
acquiring a compression plate identifier that identifies a type of a compression member attached to a mammography apparatus and an angle of an arm portion of the mammography apparatus, the mammography apparatus being configured to irradiate a breast compressed by the compression member with radiation to capture a radiographic image;

acquiring irradiation field information indicating a size of a range of an irradiation field of the radiation of the mammography apparatus, based on the compression plate identifier and the angle of an arm portion, the irradiation field information comprising information expressing a relationship of the compression plate identifier, the angle of the arm portion and the size of the range of the irradiation field; and controlling an image projection unit that projects a projection image onto a projection surface of the compression member such that a range of an irradiation field of the radiation is displayed by the projection image, in a case in which a size of a display image displayed on the projection surface by the projection image is different from the size of the range of the irradiation field indicated by the irradiation field information, wherein a display image displayed on the projection surface due to the projection of the projection image is an image larger than the range of the irradiation field on the projection surface of the compression member.

* * * * *